United States Patent [19]

McArdle

[11] Patent Number: 5,431,162
[45] Date of Patent: Jul. 11, 1995

[54] POSITIONING METHOD AND APPARATUS FOR X-RAY TOMOGRAPHY

[75] Inventor: Phillip C. McArdle, Ferntree Gully, Canada

[73] Assignee: Axialtome Australia Pty. Ltd., Ashwood, Australia

[21] Appl. No.: 179,450

[22] Filed: Jan. 11, 1994

[30] Foreign Application Priority Data

Nov. 22, 1993 [AU] Australia ............................. PM2567

[51] Int. Cl.⁶ .................................................. A61B 6/00
[52] U.S. Cl. ................................ 128/653.1; 378/162; 378/206
[58] Field of Search .................. 128/653.1; 606/130; 378/162, 170, 206

[56] References Cited

U.S. PATENT DOCUMENTS

| | | | |
|---|---|---|---|
| 4,750,487 | 6/1988 | Zanetti | 606/130 |
| 4,846,173 | 7/1989 | Davidson | 606/130 |
| 4,971,060 | 11/1990 | Schneider et al. | 128/653.1 |
| 5,068,887 | 11/1991 | Hughes | 378/206 |
| 5,165,410 | 11/1992 | Warne et al. | 128/653.1 |

FOREIGN PATENT DOCUMENTS 7904882 12/1980 Netherlands ............... 128/653.1

Primary Examiner—Ruth S. Smith
Attorney, Agent, or Firm—Feix and Feix

[57] ABSTRACT

A method and apparatus accurately positions a selected cranial implant site for x-ray tomography. The method and apparatus comprise making a stent of the mandible and maxilla of a patient and making a mark on the stent at a position which corresponds to the selected cranial implant site. The stent is then positioned with regard to a tomographic x-ray imaging apparatus so that, (a) the mark on the stent is aligned with a light beam, preferably generated by a laser source, projected downwardly to intersect the central axis of the tomographic apparatus and, (b) the selected plane through the mark is perpendicular to the x-ray beam of the tomographic apparatus.

12 Claims, 5 Drawing Sheets

POSITIONING METHOD AND APPARATUS FOR X-RAY TOMOGRAPHY

BACKGROUND OF THE INVENTION

1. Field of the invention

The present invention relates to a method and an apparatus for positioning the head of a patient accurately for tomographic x-ray imaging of a selected cross-sectional plane through the mandible or maxilla of the patient.

The method and the apparatus of the present invention are designed particularly, although by no means exclusively, for use with existing tomographic apparatus installed, for example, in dental professional offices and used for site evaluation of the mandible and the maxilla prior to installing osseointegrated implant posts to support various dental prosthesis. More particularly, the present invention is concerned with a method and an apparatus for precisely locating the patient in relation to a tomographic apparatus such that the site of the anatomy of interest is at the correct position to provide an accurate tomographic x-ray of the site.

2. Description of the Prior Art

By way of background, the dental profession has been involved to an increasing degree with the osseointegrated implant system to facilitate dental prosthesis.

In order to properly install an implant a tomographic x-ray of the proposed site should be taken so that the dentist can investigate the adequacy of the osseous tissue to support an implant post at that site. The x-ray of the mandible or maxilla should employ tomography in order to project the cross-sectional area of the mandible or maxilla at the site.

X-ray tomography involves rotating an x-ray source and a photographic plate in an arc relative to a patient during exposure of the x-ray image. Specifically, the x-ray source and the photographic plate are rotated through an arc about a central axis that is perpendicular to the x-ray beam. The result of such movement is that all bone structure in front and behind a vertical plane through the central axis are blurred and essentially do not appear in the image. The vertical plane through the central axis is hereinafter referred to as the "tomographic plane".

Thus, only that structure located at the tomographic plane appears in the x-ray image so that the image is of a cross-section of the bone tissue. Therefore, by positioning the head of a patient so that a cross-sectional area which includes a particular site of interest of the mandible or maxilla of a patient coincides with the tomographic plane it is possible to obtain an x-ray image of the particular site of interest.

Clearly, an important consideration in the use of x-ray tomography is the accurate positioning of the anatomy of interest in the tomographic plane.

U.S. Pat. No. 4,974,243 entitled "Positioning System for a X-Ray Tomography" assigned to AxialTome Corporation discloses a method and an apparatus for such accurate positioning of the head of a patient in relation to a tomographic apparatus which works effectively in many situations.

SUMMARY OF THE INVENTION

An object of the present invention is to provide an improved method and apparatus for positioning the head of a patient in relation to a tomographic apparatus.

According to the present invention there is provided a method of positioning the head of a patient accurately for tomographic x-ray imaging of a selected plane through a particular site of interest on the mandible or maxilla of the patient by means of a tomographic x-ray imaging apparatus, the x-ray tomographic imaging apparatus comprising an x-ray source that is rotatable in an arc around a central axis, the method comprising:
  (a) forming a stent of the mandible or maxilla of the patient;
  (b) marking the stent at a position on the stent which corresponds with the site of interest; and
  (c) positioning the stent with regard to the tomographic x-ray imaging apparatus so that:
    (i) the mark on the stent is aligned with a light beam projected vertically downwardly to intersect the central axis of the tomographic x-ray imaging apparatus, the light beam thereby providing an indication of the tomographic plane, as hereinbefore described, of the tomographic x-ray imaging apparatus; and
    (ii) the selected plane through the particular site of interest is perpendicular in use to an x-ray beam from the x-ray source.

It can readily be appreciated that once step (c) above has been completed, and the light source is turned off, the patient may position himself/herself to engage the stent and the tomographic x-ray imaging apparatus may be operated to produce an image of the selected plane through the particular site of interest on the mandible or maxilla of the patient. In this connection it can also readily be appreciated that the use of the stent and the light beam enables timely and accurate positioning of the patient with respect to the tomographic x-ray imaging apparatus.

It is preferred that the mark on the stent be a radio opaque marker.

It is preferred particularly that the marker be a metallic ball or other plug inserted into the stent at the site of interest.

It is preferred that the light beam be a laser beam.

It is preferred that the light beam project a cross and that the cross be oriented so that a first arm of the cross is coincident with a central axis of the x-ray beam which in use is projected from the x-ray source and a second arm of the cross is co-planar with the tomographic plane of the tomographic x-ray imaging apparatus.

It is preferred that the step of positioning the stent comprises positioning the long axis of the side of the stent that includes the mark in the stent to be parallel to the first arm of the cross.

According to the present invention there is also provided an apparatus for positioning the head of a patient accurately for tomographic x-ray imaging by means of a x-ray imaging apparatus of a selected tomographic plane through a particular site of interest on the mandible or maxilla of the patient, the tomographic x-ray imaging apparatus comprising an x-ray source that is rotatable in an arc around a central axis, the positioning apparatus comprising:
  (a) a light source for projecting a light beam vertically downwardly to intersect the central axis of the tomographic x-ray imaging apparatus, the light beam thereby providing an indication of the tomographic plane, as hereinbefore described, of the tomographic x-ray imaging apparatus; and
  (b) a means for holding and positioning the stent so that a mark on the stent that indicates the particular site of interest on the mandible or maxilla is aligned with the light beam and so that in use the selected plane through the particular site of interest is perpendicular to an x-ray beam from the x-ray source.

It is preferred that the mark on the stent be a radio opaque marker.

It is preferred particularly that the marker be a metallic ball or other plug inserted into the stent at the site of interest.

It is preferred that the light source be a laser source.

It is preferred particularly that the light source be adapted to project a cross and that the cross be oriented so that a first arm of the cross is coincident with a central axis of the x-ray beam which in use is projected from the x-ray source and a second arm of the cross is co-planar with the tomographic plane of the tomographic x-ray imaging apparatus.

It is preferred that the holding and positioning means be adapted to position the stent so that the long axis of the side of the stent that includes the mark is parallel to the first arm of the cross.

According to the present invention there is also provided a tomographic x-ray imaging apparatus for producing a tomographic x-ray image of a selected plane through a particular site of interest on the mandible or maxilla of a patient comprising, the apparatus for positioning the head of the patient accurately for tomographic x-ray imaging by means of the tomographic x-ray imaging apparatus as described in the preceding paragraphs.

BRIEF DESCRIPTION OF THE DRAWING

The method and the apparatus of the present invention is described further by way of example with reference to the accompanying drawings in which.

DESCRIPTION OF THE PREFERRED EMBODIMENT

The tomographic x-ray imaging apparatus shown in the figures comprises a column 5 with a base or floor stand 7, an arm or spar 9 (only partially shown) which is rotatable about a horizontal axis 11 (the "central axis"), an x-ray source 13 at one end of the spar 9 and an x-ray film cassette holder (not shown) at the other end of the spar 9.

In use, the tomographic x-ray imaging apparatus is operable to rotate the x-ray source 13 in an arc (typically 60°) about the central axis to produce an x-ray image of a tomographic plane extending vertically through the central axis 11. Therefore, in use, by positioning the head of a patient so that a particular site of interest on the mandible or maxilla of the patient is positioned in the tomographic plane it is possible to produce a tomographic image through that site of interest.

Figure 3:
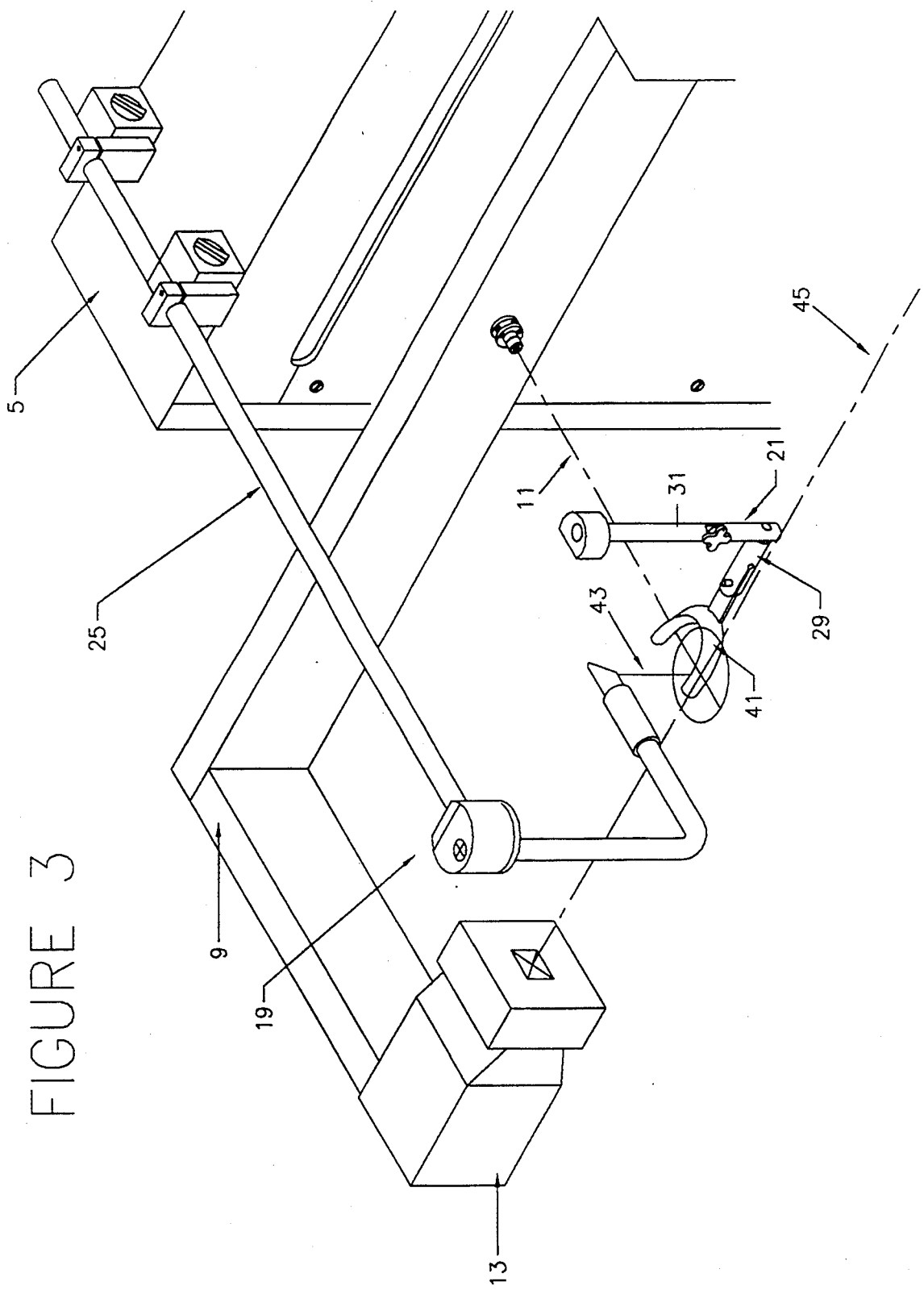
FIG. 3 is an isometric view which shows in detail the stent holder and the laser beam projection assembly which are components of the preferred embodiment of the positioning apparatus shown in FIGS. 1 and 2.

In this connection, the positioning apparatus in accordance with the preferred embodiment of the present invention is operable in relation to the tomographic x-ray imaging apparatus shown in the figures to so position the head of the patient. The positioning apparatus is based on the use of a stent 41 (FIGS. 3 and 4) of the mandible or maxilla of the patient which is marked in an appropriate way, typically by means of a radio opaque marker (not shown) such as a metallic ball, to indicate the particular site of interest.

The positioning apparatus comprises, a laser beam projection assembly, generally identified by the numeral 19, a holder 21 for securely holding a stent 41 (FIGS. 3 and 4) of the mandible or maxilla of the patient, and a positioning assembly, generally identified by the numeral 23, for effecting the necessary x-, y-, z-axis and rotational movement of the stent holder 21 and the stent 41 held at that time by the stent holder 21 to locate the stent 41 so that the area of interest of the mandible or maxilla of the patient, as represented by the stent 41, is positioned to coincide with the tomographic plane extending vertically through the central axis 11.

Figure 1:
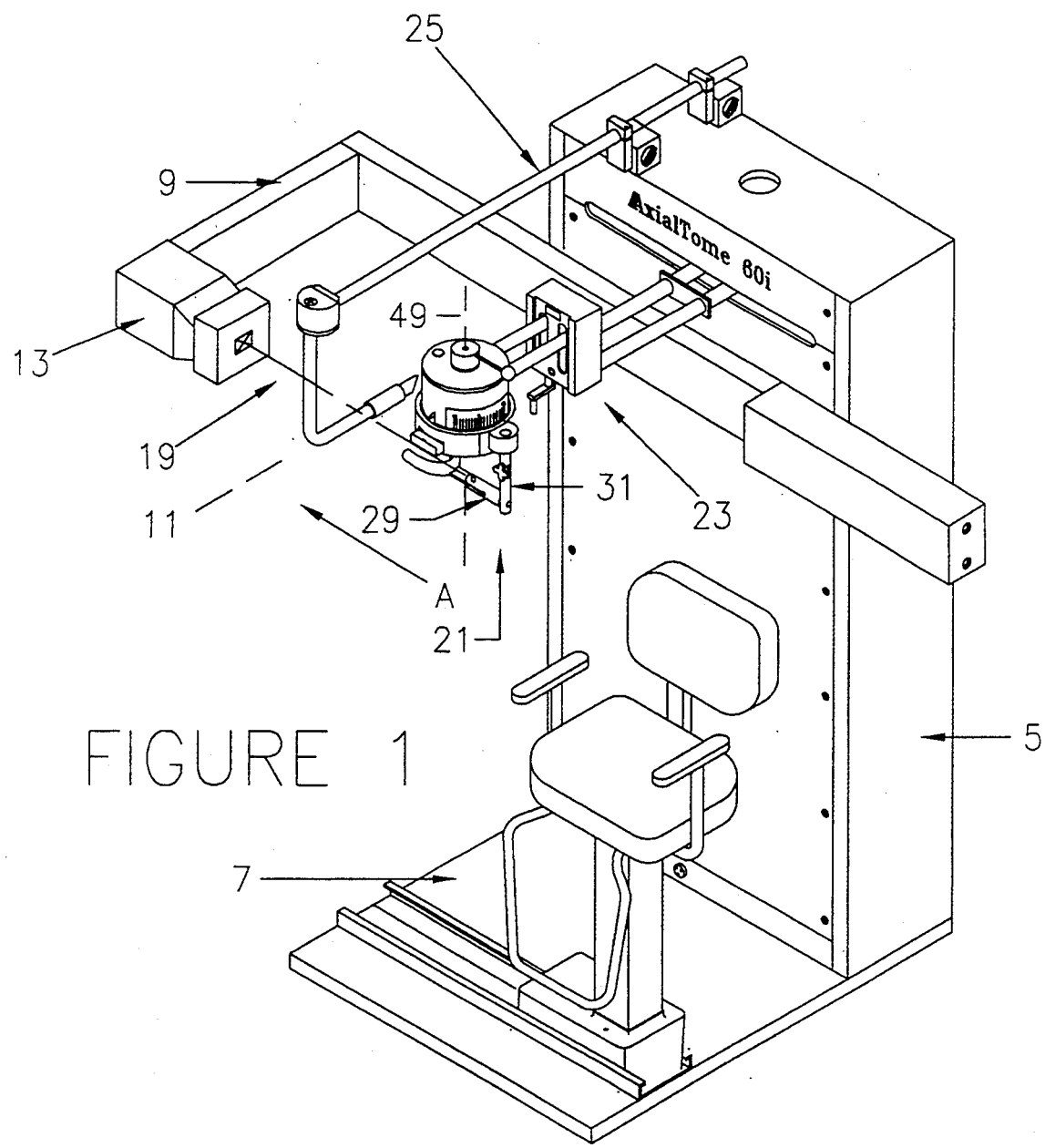
FIG. 1 is an isometric view of a tomographic x-ray imaging apparatus and a preferred embodiment in accordance with the present invention of an apparatus for positioning a head of a patient accurately in relation to the tomographic x-ray imaging apparatus.
Figure 2:
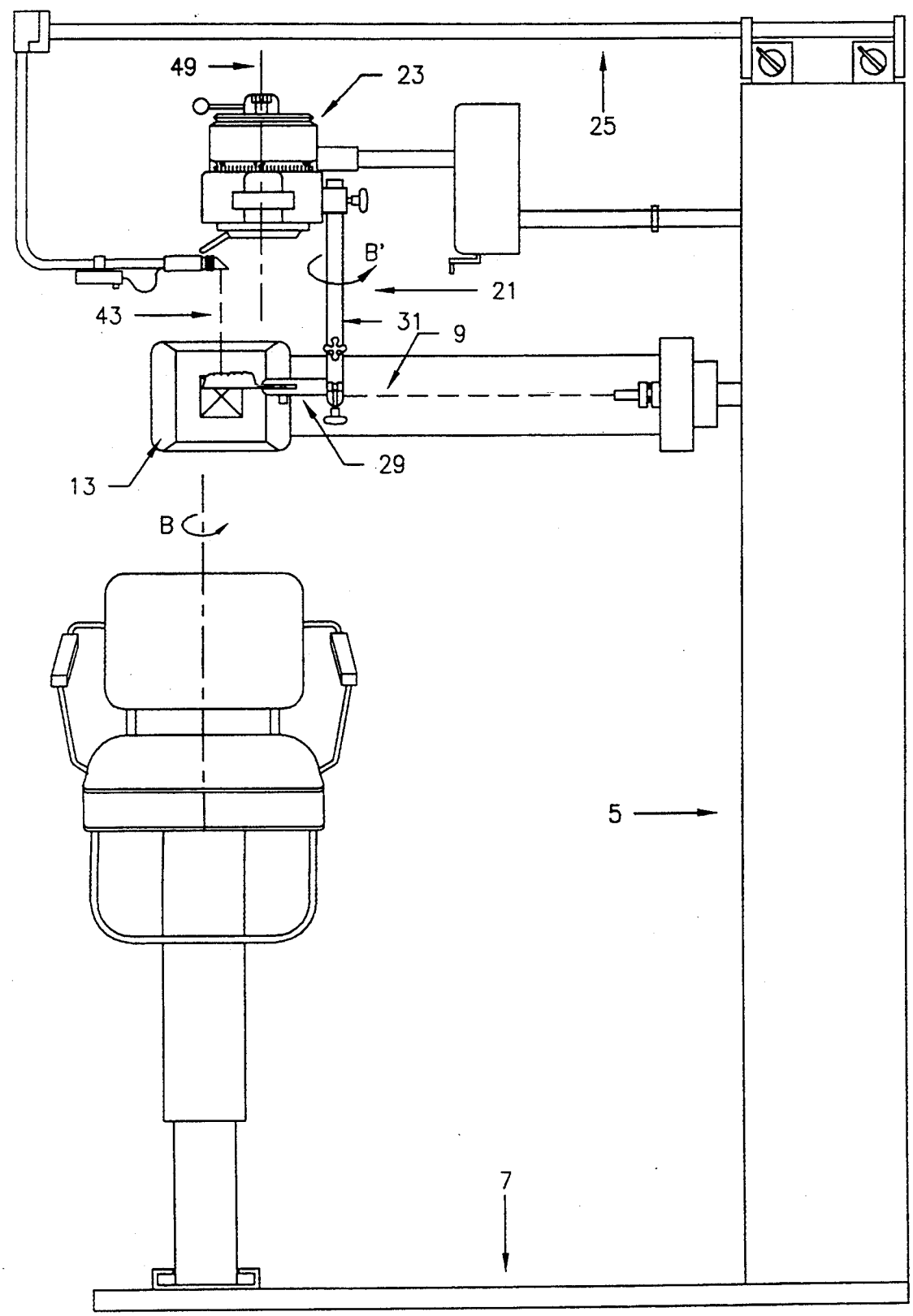
FIG. 2 is an elevation of the apparatus shown in FIG. 1 when viewed in the direction of the arrow A in FIG. 1 and shown with the chair and clamping member 29 rotated ninety degrees in the counter clockwise direction as indicated by arrows B and B', respectively.

The laser beam projection assembly 19 comprises a laser source (not shown) and a support arm 25 arranged so that, in use, the laser source projects a laser beam 43 (FIGS. 2 and 3) vertically downwardly in the tomographic plane to intersect a central axis 45 (FIG. 3) of the x-ray beam from the x-ray source 13. It can readily be appreciated that the laser beam 43, so projected, provides a readily identifiable visual indication of the location of the tomographic plane.

In the preferred embodiment of the apparatus of the present invention, the laser beam is projected in the form of a cross which is oriented so that a first arm is parallel to the central x-ray axis 45 and a second arm is co-planar with the tomographic plane. In this connection, it can readily be appreciated that the laser beam, when projected onto the surface of the stent 41 provides a readily identifiable means of assessing the position of the stent 41 with respect to the marking on the stent 41 which indicates the particular site of interest of the mandible or maxilla of the patient.

Figure 4:
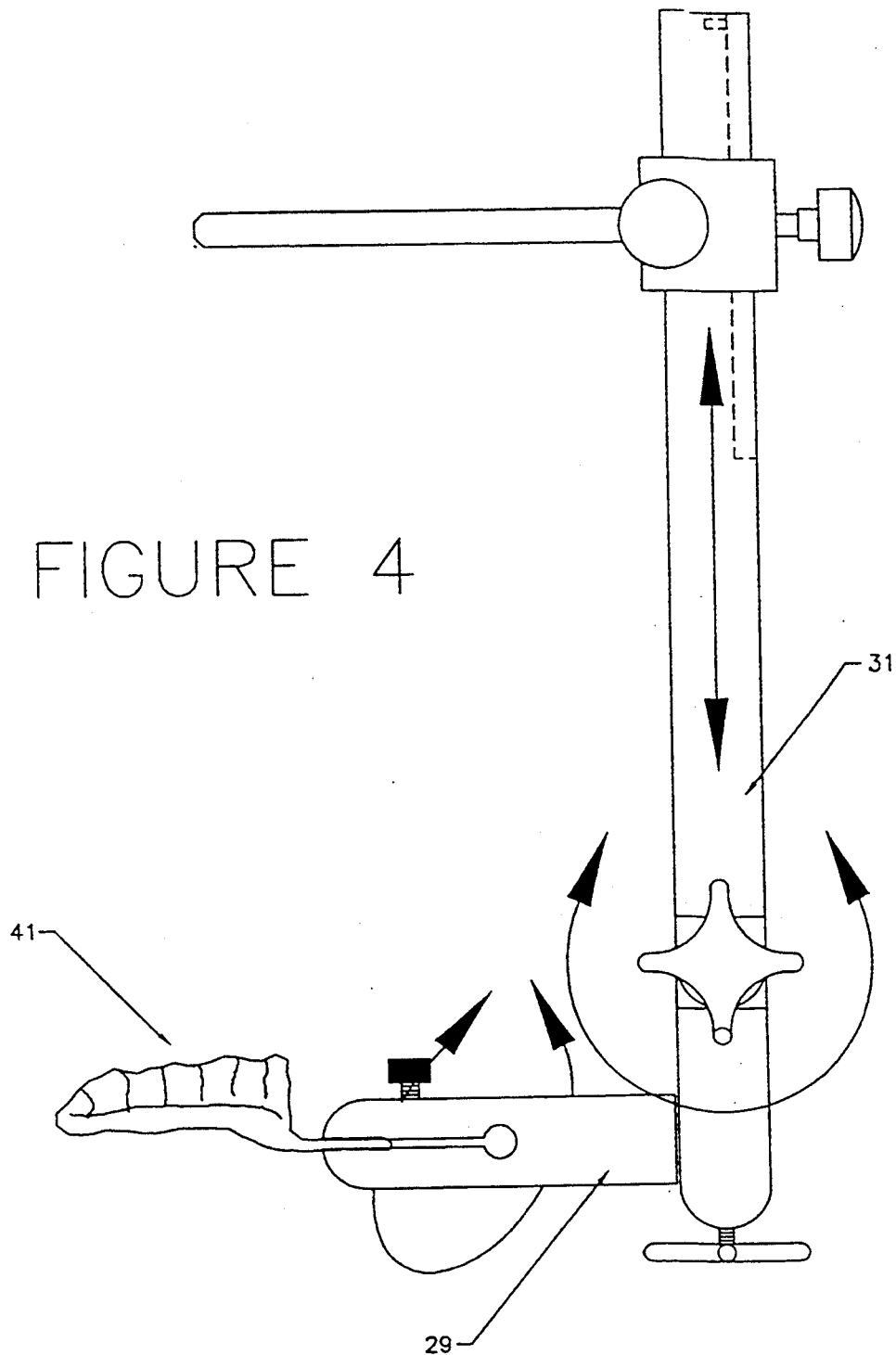
FIG. 4 is an elevation of the stent holder shown in FIGS. 1 to 3.
Figure 5:
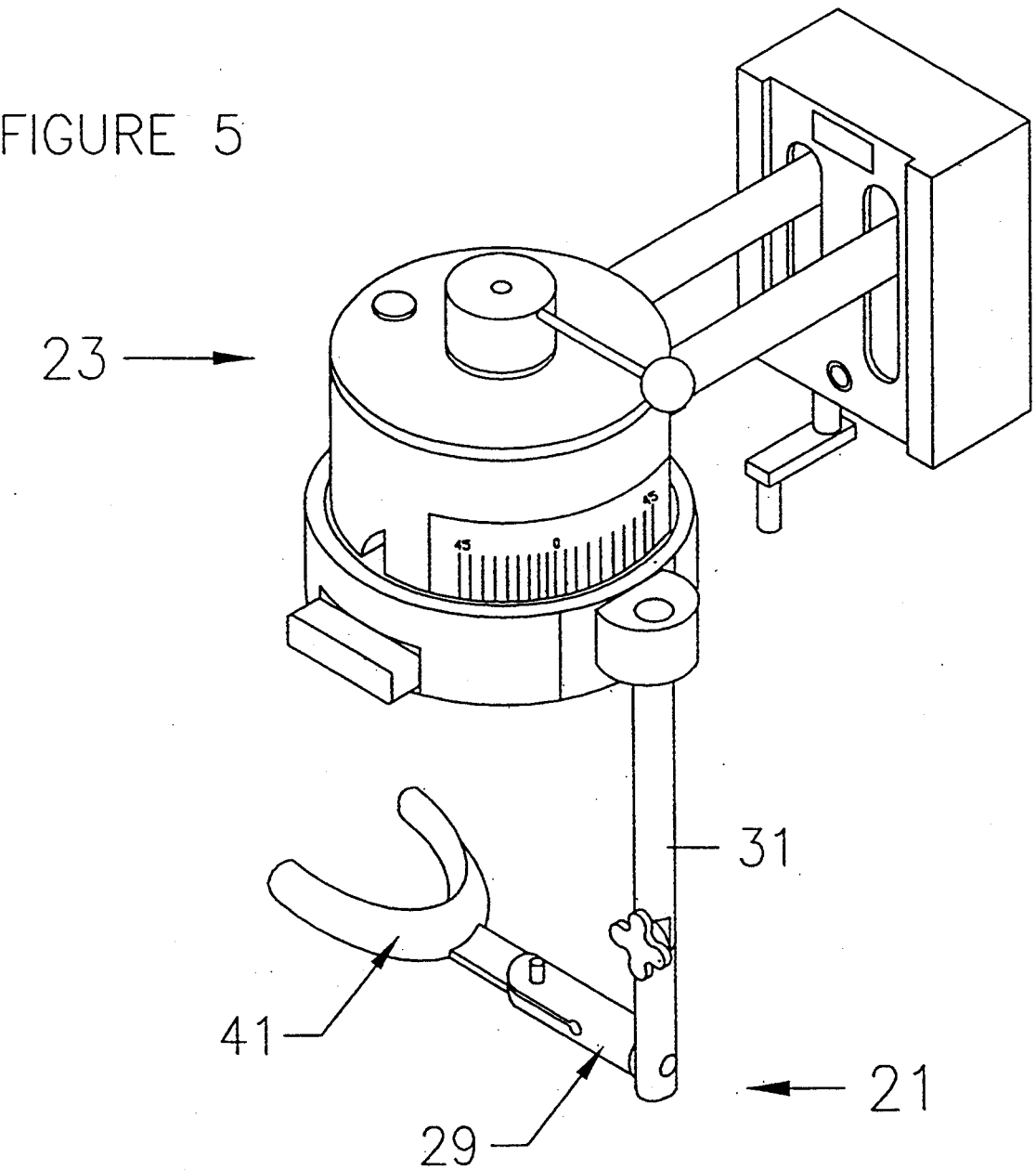
FIG. 5 is an isometric view which shows in detail the Wehmer Cephalostat which is a further component of the preferred embodiment of the position apparatus shown in FIGS. 1 and 2 and which was omitted from FIG. 3 for clarity reasons.

With particular reference to FIG. 4, the stent holder 21 comprises a clamping member 29 for clamping securely the stent 41 of a patient and a vertically extending support arm 31 which, at an upper end, is detachably mounted to the positioning assembly 23. The stent holder 21 is formed to allow selected vertical adjustment of the stent 41 with respect to the positioning assembly 23.

The positioning assembly 23, in the preferred embodiment shown in the figures, comprises a Wehmer Cephalostat, of generally conventional configuration, which is mounted to the column 5 and supports the stent holder 21 and enables positioning of the stent 41 by movement in the x-, y-, and z-axes and rotation about a vertical axis 49.

in use of the apparatus described above, a clinician prepares a stent 41 of the mandible or maxilla of a patient and marks the stent 41 in an appropriate manner to indicate the location of a particular site of interest on the mandible or maxilla, for example for an osseointegrated implant post, and then locates the stent 41 in the stent holder 21. The clinician thereafter manipulates the positioning assembly 23 to position the stent 41 so that the metallic ball or other marking in the stent 41 is aligned with the downwardly projected laser cross. The laser beam is then turned off and the patient positions himself/herself to engage the stent 41 and by so doing positions the particular site of interest on the mandible or maxilla in the tomographic plane. The clinician then operates the tomographic apparatus so that a x-ray image of the tomographic plane, and thereby the particular site of interest, is produced. By inspection of the x-ray image the clinician can determine whether the particular site of interest is acceptable for receiving an osseointegrated implant post.

Many modifications may be made to the preferred embodiment of the method and apparatus of the present invention as described above without departing from the spirit and scope of the present invention.

For example, whilst the preferred embodiment of the apparatus includes the use of a Wehmer Cephalostat it can readily be appreciated that the present invention is not so limited and any suitable means for positioning a stent may be used.

What is claimed is:

1. A method of positioning the head of a patient accurately for tomographic x-ray imaging of a selected plane through a particular site of interest on the mandible or maxilla of the patient by means of a tomographic x-ray imaging apparatus, the x-ray tomographic imaging apparatus comprising an x-ray source that is rotatable in an arc around a central axis that is perpendicular to an x-ray beam emitted from the x-ray source, the central axis lies within a vertical plane which defines a tomographic plane of the x-ray imaging apparatus, the method comprising the steps of:
   (a) forming a stent of the mandible or maxilla of the patient;
   (b) marking the stent at a position on the stent which corresponds with the site of interest;
   (c) projecting a light beam vertically downwardly onto the stent;
   (d) positioning the stent with regard to the tomographic x-ray imaging apparatus so that:
     (i) the mark on the stent is aligned with the vertically downwardly projected light beam such that the light beam intersects a central axis of the tomographic x-ray imaging apparatus, the light beam thereby providing an indication of the tomographic plane of the tomographic x-ray imaging apparatus;
     (ii) the selected plane through the particular site of interest is perpendicular to the x-ray beam from the x-ray source;
   (e) turning off the light beam;
   (f) positioning the head of a patient to engage the stent; and
   (g) operating the tomographic x-ray imaging apparatus to produce an x-ray image of the selected plane through the particular site of interest which corresponds to the mandible or maxilla of the patient.

2. The method defined in claim 1, wherein the step of marking the stent includes using a radio opaque marker.

3. The method defined in claim 1, wherein the step of marking the stent includes inserting a metallic plug into the stent at the site of interest.

4. The method defined in any one of claims 1 to 3, wherein the step of projecting a light beam includes projecting a cross having a first arm coincident with a central axis of the x-ray beam and a second arm co-planar with the tomographic plane of the tomographic x-ray imaging apparatus.

5. The method defined in claim 4, which includes using a laser to project the cross.

6. The method defined in claim 5, wherein the step of positioning the stent comprises positioning the long axis of the side of the stent that includes the mark in the stent to be parallel to the first arm of the cross.

7. In combination, a tomographic x-ray imaging apparatus comprising an x-ray source the x-ray source being rotatable in an arc around a central axis perpendicular to an x-ray beam emitted from x-ray source, the central axis lying within a vertical plane which defines a tomographic plane of the tomographic x-ray imaging apparatus, and an apparatus for positioning the head of a patient accurately for tomographic x-ray imaging of a selected tomographic plane through a particular site of interest on the mandible or maxilla of the patient, the positioning apparatus comprising:
   (a) light source means for projecting a light beam vertically downwardly to intersect the central axis of the tomographic x-ray imaging apparatus, the light beam thereby providing an indication of the tomographic plane of the tomographic x-ray imaging apparatus;
   (b) a stent of the mandible or maxilla of a patient, said stent having a mark corresponding to a site of interest on the mandible or maxilla; and
   (c) a means for holding and positioning the stent so that the mark on the stent is aligned with the light beam such that when the patient is positioned to engage the stent and the x-ray imaging apparatus is operated to produce an x-ray image, the selected plane through the particular site of interest is perpendicular to the x-ray beam from the x-ray source.

8. The apparatus defined in claim 7, wherein the mark on the stent is a radio opaque marker.

9. The apparatus defined in claim 8, wherein the radio opaque marker is a metallic plug inserted into the stent at the particular site of interest.

10. The apparatus defined in any one of claims 7 to 9, wherein the light beam projected by the light source means is formed as a cross and the cross is oriented so that a first arm of the cross is coincident with a central axis of the x-ray beam from the x-ray source and a second arm of the cross is co-planar with the tomographic plane of the tomographic x-ray imaging apparatus.

11. The apparatus defined in claim 10, wherein the light source means comprises a laser source.

12. The apparatus defined in claim 11, wherein the holding and positioning means is adapted to position the stent so that the long axis of the side of the stent that includes the mark is parallel to the first arm of the cross.

* * * * *